United States Patent
Rao

(10) Patent No.: US 10,648,980 B2
(45) Date of Patent: May 12, 2020

(54) IGG SUBTYPING ASSAY FOR IDENTIFYING TRANSPLANTABLE TISSUE SAMPLES

(71) Applicant: New Jersey Organ and Tissue Sharing Network, Inc., New Providence, NJ (US)

(72) Inventor: Prakash Rao, Green Brook, NJ (US)

(73) Assignee: New Jersey Organ and Tissue Sharing Network, Inc., New Providence, NJ (US)

( * ) Notice: Subject to any disclaimer, the term of this patent is extended or adjusted under 35 U.S.C. 154(b) by 268 days.

(21) Appl. No.: 15/369,097

(22) Filed: Dec. 5, 2016

(65) Prior Publication Data

US 2017/0160278 A1    Jun. 8, 2017

Related U.S. Application Data

(60) Provisional application No. 62/262,636, filed on Dec. 3, 2015.

(51) Int. Cl.
| | | |
|---|---|---|
| G01N 33/569 | (2006.01) | |
| G01N 33/68 | (2006.01) | |
| A61K 35/22 | (2015.01) | |
| A61K 35/34 | (2015.01) | |

(52) U.S. Cl.
CPC ....... *G01N 33/56972* (2013.01); *A61K 35/22* (2013.01); *A61K 35/34* (2013.01); *G01N 33/6854* (2013.01)

(58) Field of Classification Search
None
See application file for complete search history.

(56) References Cited

U.S. PATENT DOCUMENTS

| | | |
|---|---|---|
| 2010/0261203 A1 | 10/2010 | Cicciarelli |
| 2011/0281757 A1 | 11/2011 | Tan |
| 2014/0170169 A1 | 6/2014 | Cicciarelli |

OTHER PUBLICATIONS

Karuppan et al. (Transplantation, (Nov. 1992) vol. 54, No. 5, pp. 839-844. (Year: 1992).*
Innovex (Fc Receptor Blocker, Jan. 2015, pp. 1-2). (Year: 2015).*
"Fc Receptor Blocker Peptide-Based Technology" website of Innovex, copyright 2012, pp. 1-3. (Year: 2012).*
Prabhu et al., PLoS ONE 11(9): e0162242, Sep. 1-17, 2016. (Year: 2016).*
Smirnova et al., Altex 32(4), 2015, pp. 247-260. (Year: 2015).*
Scornik (Cytometry, 22:259-263 (1995)) (Year: 1995).*
International Search Report and Written Opinion for related application PCT/US16/64933, dated Feb. 28, 2017.
Khovanova et al., 2015, Translpant Intl. 28:1405-1415.
Muthana et al., 2015, PLOS One, 10(3):e0119298.
Hogarth et al., 2012, Nature Rev. 11:311-331.
Santos et al., 2014, In: Weir et al. eds., Kidney Transplantation: Practical Guide to Management, Springer Science + Business Media, New Yourk, pp. 23-34.
Bose et al., 2013, Transplantation Antigens and Histocompatibility Matching, Chpt. 17, http://dx.doi.org/10.5772/54738, accessed on Oct. 30, 2015.
Gao et al., 2004, Liver Transplant. 10:1055-1059.
Gao et al., 2014, Am. J. Transplant. 14:1581-1591.
Kaneku et al., 2012, Liver Transplant. 18:984-992.
Mulley et al., 2011, Nephrology 16:125-133.

* cited by examiner

*Primary Examiner* — Zachary S Skelding
(74) *Attorney, Agent, or Firm* — Preti Flaherty Beliveau & Pachios LLP

(57) ABSTRACT

The disclosure relates to methods for assessing the suitability of a tissue obtained from a vertebrate (e.g., human) donor for grafting to a recipient, such as another vertebrate of the same species. The method involves contacting leukocytes obtained from the donor with serum from the recipient. Binding between recipient antibodies and the leukocytes is assessed, specifically focusing on the subtype(s) of IgG antibodies which bind with donor leukocytes. Detected binding between recipient antibodies of subtypes IgG1 and IgG3 indicates that the donor tissue is not suitable for grafting to the recipient. Detected binding between recipient antibodies of subtypes IgG2 and/or IgG4 indicates that the donor tissue can suitably be grafted to the recipient.

13 Claims, 2 Drawing Sheets

| # | Recipient Name | FCXM | C1q | B cells IgG 1 | IgG 2 | IgG 3 | IgG 4 | T cells IgG 1 | IgG 2 | IgG 3 | IgG 4 | Pre-txp. Cr. | Post-txp. Cr. | Induction | Maint. Immuno Meds | Dialysis First Week | Rejection Episodes |
|---|---|---|---|---|---|---|---|---|---|---|---|---|---|---|---|---|---|
| 1 | KR | NEG | NEG | + | + | + | + | + | +++ | + | + | 4.1 | 1.48 | thymo induction | tacrolimus, mycophenolate mofetil | No | No |
| 2 | CFL | NEG | NEG | + | + | +++ | + | + | +++ | + | + | 6.1 | 0.77 | thymo induction | tacrolimus, myfortic | No | No |
| 3 | IA | POS | NEG | + | + | + | + | + | +++ | + | + | 7.55 | 1.96 | thymo induction | tacrolimus, myfortic | No | No |
| 4 | GS | POS | NEG | + | + | + | + | + | + | + | + | 8.3 | 1.48 | thymo induction | tacrolimus, myfortic | No | No |
| 5 | BJ | POS | NEG | + | + | + | + | + | + | + | + | 5.06 | 6.75 | thymo induction | tacrolimus, myfortic | No | No |
| 6 | TD | POS | NEG | + | + | + | + | + | + | + | + | 9.15 | 2.33 | thymo induction | tacrolimus, myfortic | No | No |
| 7 | CF | POS | POS | + | + | +++ | + | + | + | + | + | 3.2 | 0.82 | thymo induction | tacrolimus, myfortic | No | No |

+ Baseline IgG subtypes detected in Pt sera against respective donor cells
+++ These are the Positive IgG subtypes detected in Pt sera against respective donor cells
All values are Fold increase above Negative Control Serum

IGG SUBTYPING ASSAY FOR IDENTIFYING TRANSPLANTABLE TISSUE SAMPLES

CROSS-REFERENCES TO RELATED APPLICATIONS

This application is entitled to priority to U.S. provisional patent application No. 62/262,636 filed 3 Dec. 2015.

BACKGROUND OF THE DISCLOSURE

The invention relates generally to the field of organ and tissue transplantation, and more specifically to procedures for matching donor tissues and recipients whose bodies will not reject the tissue if transplanted into the recipient.

Transplantation of organs and tissues from the body of a donor into the body of a recipient has become a relatively common procedure. Owing to fundamental functions of the immune system of vertebrates (i.e., to alert the body to "non-self" materials and to assist in elimination of such non-self materials), tissues cannot be simply transplanted from the body of one individual of a given species into the body of any other individual of the same species without the possibility of immune complications. If the transplanted tissue is not compatible with the immune system of the recipient, the recipient's immune system can mount a response against the transplanted tissue whereby the transplanted tissue is destroyed. In order to avoid such transplant rejection, two basic strategies can be employed. First, one or more immune functions of the recipient can be inhibited, so as to lessen or eliminate the immune response mounted against the transplant. Second, the transplant and recipient can be screened and matched, to lessen the likelihood and/or severity of a recipient immune response against the transplant. The subject matter described herein is directed primarily toward this second strategy, although the two strategies are not mutually exclusive—both can be employed in the same transplantation.

It has long been known that cells in vertebrate tissues express antigens on their surface, and that these antigens can vary significantly among individuals of the same species. For example, human cells display proteins designated human leukocyte antigens (HLAs) on their surfaces. For any individual human, the HLAs displayed by that individual's cells are recognized as "self" by the individual's immune system, and the individual's immune system does not (normally) mount an immune response against his or her own cells. However, the HLAs displayed by different individual humans can vary significantly enough that HLAs not normally expressed by an individual's cells, such as HLAs of transplanted tissue, can be recognized as "non-self" by an individual's immune system, leading to initiation of an immune response directed against the transplanted tissue. If the immune response initiated against a transplanted tissue is sufficiently severe to induce death of most or all transplanted cells or destruction of sufficient transplanted extracellular material, the transplanted tissue can fail to exhibit desirable functions or properties that were the reason for the transplant. That is, the goals which led to the transplantation can fail to be achieved if the recipient immune response mounted against the transplanted tissue is sufficiently severe.

One type of immune response that a recipient's body can mount against a transplanted tissue depends on binding of antibodies produced by the recipient's body to antigens (e.g., HLAs) that are displayed on surfaces of the transplanted tissue. Specific binding between antibodies and their corresponding antigens can catalyze a reaction ("complement fixation") that leads to induction of a potent cytotoxic immune response directed against the transplanted tissue. Analyzing the ability of recipient immune system components to detect donor tissue as "non-self" and mount a cytotoxic response and selecting donor-recipient pairs to avoid such reactions is referred to generally as "crossmatching" and is discussed extensively in the literature (see, e.g., Mulley et al., 2011, Nephrology 16:125-133).

One known crossmatching technique involves contacting lymphocytes obtained from the donor of a potential transplant tissue with blood serum obtained from a proposed recipient of the transplant tissue. Serum includes antibodies which circulate in the blood of the recipient. If the recipient's serum includes antibodies which bind specifically with antigens which appear on donor lymphocytes, such binding can be detected. In one common detection technique known as "flow crossmatching," donor lymphocytes are contacted with recipient serum for a period of time, after which non-bound antibodies are removed by separating the lymphocytes and serum and rinsing the lymphocytes with an excess reagent. The lymphoctyes are then contacted with a labeled reagent capable of detecting recipient antibodies (e.g., a fluoresceinated antibody which binds to human antibodies, optionally of a particular type, such as IgM or IgG, or subtype, such as IgG1, IgG2, IgG3, or IgG4) and thereafter rinsing non-bound labeled reagent from the lymphocytes. Binding of recipient antibodies with donor lymphocytes is detected by suspending the lymphocytes in a fluid and passing them through a flow cytometer capable of detecting the label of the labeled reagent. Detection of the label together with a lymphocyte by the flow cytometer (e.g., detection of fluorescence corresponding to fluorescein) indicates that one or more recipient antibodies recognized by the labeled reagent is bound to the lymphocyte. Such bound recipient antibodies are commonly designated "anti-donor antibodies" (ADAbs). If multiple flow crossmatching reactions are performed, each using a labeled reagent having specificity for a different recipient antibody type and/or subtype, a profile of the type(s) and subtypes(s) of ADAbs that are present in an potential recipient's serum can be developed.

It has been observed that ADAb types and subtypes can influence the likelihood that a transplanted tissue will be rejected by a recipient. Mulley et al., for example, recognized that IgG4 does not activate complement and that potential recipients whose ADAb detected using donor leukocytes are solely of the IgG4 subtype may be less likely to activate complement in vivo (i.e., indicating a potentially suitable donor-recipient match). Comparable observations were reported by Cicciarelli et al. (U.S. patent application publication no. 2010/0261203). Gao et al. (2014, Am. J. Transplant. 14(7):1581-1591) recognized that IgG antibodies of subtypes IgG1 and IgG3 which react with apoptotic cells are more likely to lead to late rejection of transplanted kidneys, presumed by those authors to be attributable to the complement-fixing ability of IgG1 and IgG3 subtypes. However, previous workers examined binding between antigen-coated beads and antibodies in recipient serum, which assays can be laborious and not necessarily indicative of interactions between recipient antibodies and donor cells.

Improved crossmatching assays capable of quickly and accurately determining the suitability of a potential tissue transplant for implantation in (or on) an individual recipient would be desirable. This disclosure describes such assays.

BRIEF SUMMARY OF THE DISCLOSURE

The invention relates to methods of assessing compatibility of a body tissue of a potential donor for grafting with a recipient. The methods involve contacting leukocytes obtained from the potential donor with antibodies obtained from the recipient. Binding between the potential donor leukocytes and recipient antibodies is assessed for at least IgG subtypes IgG1 and IgG3. The body tissue is assessed as compatible for grafting with the recipient if substantially no binding between the donor leukocytes and recipient antibodies of either of IgG subtypes IgG1 and IgG3 is detected. The invention also involves tissue grafting procedures which include such assessment methods.

In the assessment methods, binding between the donor leukocytes and recipient antibodies is preferably assessed for each of at least IgG subtypes IgG1, IgG2, IgG3, and IgG4, preferably using differentially-labeled antibodies that distinguishably recognize the subtypes, and preferably in a single assay mixture. If desired, the assessment methods can also include contacting the donor leukocytes with differentially-labeled antibodies that distinguishably recognize B and T cells of the donor. Individual donor leukocytes and the antibodies and/or labels bound to them can be assessed by flow cytometry after contacting the donor leukocytes with the recipient antibodies.

The assessment methods are suitable for use with recipients which are vertebrates, preferably being a human.

Non-specific binding between recipient antibodies and Fc receptors on donor leukocytes can inhibited using known reagents. The donor leukocytes are preferably alive at the time they are contacted with the antibodies obtained from the recipient.

BRIEF SUMMARY OF THE SEVERAL VIEWS OF THE DRAWINGS

FIG. 1 is a table illustrating results of experimental results described in Example 5 herein.

FIG. 2 is a table illustrating results of experimental results described in Example 6 herein.

DETAILED DESCRIPTION

The disclosure relates to methods for crossmatching tissue from a donor with a suitable recipient for the tissue. The methods involve determining anti-donor IgG subtype(s) present in a sample that contains antibodies obtained from the recipient, such as serum prepared from the blood of the recipient.

The donor tissue can be tissue that has already been collected (and potentially stored and/or frozen) from a living or recently deceased vertebrate, such as a human donor, or it can be tissue that remains a part of a donor candidate. In any of these circumstances, the individual from whom, or from whose corpse, the tissue has been collected or may in the future be collected is referred to herein as the "donor." The crossmatching method will normally be performed after the donor tissue has been collected from the donor; however, the method can be performed prior to collecting the tissue to be transplanted (e.g., if that tissue will not be collected if the recipient is not a suitable recipient for it) by testing leukocytes obtained from the donor against IgG antibody subtypes in serum obtained from a candidate recipient (i.e., and foregoing harvesting of the tissue if anti-donor IgG1 or IgG3 antibody subtypes are detected in the candidate recipient's serum). Potential donor leukocytes can be frozen and archived, optionally together with or within a stored donor tissue.

The method involves contacting leukocytes (e.g., peripheral blood mononuclear cells) obtained from the donor with antibodies in a sample (e.g., blood serum) obtained from the a potential recipient of the donor's tissue and there after detecting—in a single assay—whether antibodies (Abs) of multiple IgG subtypes present in the recipient's sample have bound to the donor's leukocytes. This assessment is preferably performed by flow cytometry using reagent that contains a plurality of differentially-labeled Abs, each of which binds specifically to only certain subtypes (preferably only to a single subtype) of IgG antibodies. Such differentially-labeled Abs are described herein as "distinguishably recognizing" the various subtypes of IgG antibodies. After excess reagent is separated from the leukocytes, the leukocytes are assessed, by flow cytometry for example, to detect any label(s) associated with the leukocytes. From this information, it can be determined which donor-leukocyte-binding IgG subtypes are present in the recipient's serum. If desired, the various donor leukocytes can be distinguished from one another, such as by known flow cytometric methods, by labeling them with one or more Abs which distinguishably recognize (i.e., can be used to distinguish) T and B cells. In the assay described herein, binding of recipient IgG1 and/or IgG3 antibodies with donor T cells generally indicates a less favorable match than does the same binding with donor B cells, although both types of binding indicate a less favorable match than does the absence of both types of binding.

Recipient antibodies can be obtained from the recipient's blood, such as by isolating blood serum (i.e., the cell-free fluid component of blood) therefrom. Recipient antibodies can also, or alternatively, be used in or isolated from any other body fluid or wash/lavage fluid known or believed to contain antibodies that are representative of the patient's body. By way of example, recipient antibodies can be obtained from a pleural aspirate, a bronchial lavage, or a peritoneal fluid sample. Regardless of how the recipient antibody-containing sample is obtained or prepared, it is important that IgG antibodies (at least of the IgG1 and/or IgG3 subtypes) that are present in the sample be treated and/or stored in ways which preserve the ability of IgG1 and or IgG3 antibodies therein to bind with the donor's leukocytes. A preferred sample of recipient antibodies is blood serum.

If the recipient's sample contains donor-leukocyte-binding IgG Abs of the IgG1 or IgG3 subtypes, the potential recipient is likely not a suitable recipient for the donor's tissue, and the donor's tissue should not be grafted with the donor. Occurrence of anti-donor IgG1 or IgG3 subtypes in the recipient's sample is an indication that graft-rejection symptoms are likely to occur if a tissue from the donor is transplanted to the recipient. That is, such occurrence indicates that antibody-mediated rejection is more likely to occur than if the recipient's sample does not contain anti-donor IgG1 or IgG3 subtypes. The likelihood of graft-rejection symptoms can also be at least roughly correlated with increasing degree of detection of IgG1 and/or IgG3. Thus, for example, an individual whose leukocytes provoke relatively low levels of binding of recipient IgG1 and/or IgG3 antibodies in the assay described herein would be considered a preferable tissue donor than another individual whose leukocytes provoke a substantially higher level of binding of recipient IgG1 and/or IgG3 antibodies in that assay. Also, given the known greater propensity of IgG3 to induce complement fixation, detection of a given level of recipient-IgG3 binding with donor leukocytes (e.g., two-fold above normal background level) is considered an indication of a less favorable donor match than detection of the same level of recipient-IgG1 binding with the donor's leukocytes. In general, detection of recipient-IgG3 or -IgG1 binding with donor leukocytes greater than about two-fold greater than the basal (i.e., normal background) level of such binding is considered indicative of an unfavorable donor match (i.e., increased likelihood of graft-rejection symptoms), with greater detected binding generally indicating a more-unfavorable donor match.

If the recipient's sample does not contain donor-leukocyte-binding IgG Abs of the IgG1 or IgG3 subtypes, the potential recipient likely is a suitable recipient for the donor's tissue, and the donor's tissue can be grafted to the recipient with a reasonable expectation that it will not be rejected, at least by physiological processes involving complement fixation.

The methods described herein are therefore useful for determining whether an individual recipient can be expected to reject a tissue obtained from a different individual donor (of a different or, preferably, the same species). A recipient can be expected to reject a tissue obtained from a donor if the recipient's sample includes donor-leukocyte-binding antibodies of subtypes IgG1 or IgG3, and can be expected not to reject the tissue if the donor's sample does not include donor-leukocyte-binding antibodies of subtypes IgG1 or IgG3 (even if the donor's sample includes donor-leukocyte-binding antibodies of subtypes IgG2 and/or IgG4).

In contrast to prior methods, the methods described identify not only likely-successful tissue grafts which could be identified using prior methods that relied on detection of donor-leukocyte-binding antibodies of IgG of undifferentiated subtypes, but also additional likely-successful tissue grafts which could not be identified using those prior methods.

The present methods have the advantage that multiple assessments (e.g., detection of IgG1 and detection of IgG3) can be performed in a single reaction mixture, using a single aliquot of sample. Because all of the multiple assessments are performed using the same sample, difficulties which can arise from reliance of multiple assays on multiple corresponding controls are avoided.

The present methods have the additional advantage that they are performed using whole donor cells, rather than synthetic beads to which donor antigens are attached. Donor cells (e.g., live PBMCs) can be expected to closely mimic antigen presentation by donor tissue; by contrast, synthetic beads bearing donor antigens may present donor antigens substantially differently than the manner in which those same antigens are presented by donor tissue. Thus, the methods described herein can be expected to be more accurately predictive of recipient responses to donor tissue.

Use of the methods described herein for matching human recipients with human donors of tissues is intended. However, it is also understood that the same methods, with merely routine modifications, can be used to match individual recipients of substantially any vertebrate species with donors of tissues of the same species. Likewise, the same methods, with routine modifications, can be used to match individual recipients of a first vertebrate species with tissues obtained from donors of a second, different vertebrate species (although it is recognized that other assays for recipient appropriateness would likely be conducted for inter-species tissue transfers).

EXAMPLES

The subject matter of this disclosure is now described with reference to the following Examples. These Examples are provided for the purpose of illustration only, and the subject matter is not limited to these Examples, but rather encompasses all variations which are evident as a result of the teaching provided herein.

Example 1

Isolation of PBMCs from Donor Blood

Peripheral Blood Mononuclear Cells (PBMCs, which include both lymphocytes and monocytes) were isolated from donor whole blood that was collected in acid citrate dextrose (ACD) vacutainer tubes. Donor blood was transferred to 15 milliliter conical tubes and mixed with 2 milliliters methyl cellulose (1% solution, weight/volume; Sigma-Aldrich, St. Louis, Mo., USA) by inversion. The tube was rotated in a 37 degrees Celsius incubator for 15 minutes and left standing at 37 degrees Celsius for an additional 30 minutes to separate the plasma layer containing enriched lymphocytes from the red blood cells layer. The plasma layer was carefully transferred to a fresh 15 milliliter conical tube and diluted with dulbecco's phosphate-buffered saline (DPBS, Lonza, Walkersville, Md., USA) at a ratio of 1:1 (plasma:DPBS) and mixed by inversion.

Using a Pasteur pipette, the diluted plasma was underlaid with lymphocyte separation medium (LSM) such that the ratio of diluted plasma:LSM was 1:1. The tube was centrifuged at 22 degrees Celsius in a swing bucket rotor at 400×g for 25 minutes with slow deceleration. The clear white band at the interface containing PBMCs was transferred to a fresh 15 milliliter conical tube and diluted with DPBS to a final volume of 10 milliters. The tube was centrifuged at 260×g for 10 minutes at 22 degrees Celsius to pellet the PBMCs. The supernatant containing platelets was discarded, leaving the pellet rich in PBMCs. The pellet was carefully resuspended in 2 milliliters DPBS, and the cells were counted in a hemocytometer using 1:2 dilution of Trypan Blue.

IgG Subtype Assay

IgG subtype analysis was carried out using the highly sensitive flow-cytometry crossmatch (FCXM) platform, as follows. Briefly, PBMCs isolated from the donor blood were aliquoted into separate 5 milliliter polystyrene round bottom tubes at a concentration of $5 \times 10^5$ cells/tube. The cells were washed with DPBS and pelleted by centrifugation at 800×g for 5 minutes at 22 degrees Celsius. The FC receptors on the cell surface were blocked using Fc Receptor Blocker reagent (obtained from Innovex Biosciences, Richmond, Calif., USA) for 10 minutes at room temperature (ca. 20 degrees Celsius). The blocking reagent was removed by washing the cells twice with DPBS followed by incubation with patient (i.e., recipient) serum for 30 minutes at 4 degrees Celsius. Donor cells were also incubated with negative and positive control serum samples. Positive control sera were prepared by pooling sera from five patients who were highly sensitized (each having cPRA values greater than 98%). This positive sera reacts with PBMC cells from all donors yielding consistently positive FCXM results. Negative control sera (obtained from Gemini Bio-Products, West Sacramento, Calif., USA) was collected from healthy male donors of the AB serotype at FDA-licensed facilities in the United States. This material is defibrinated from source plasma AB. All donor units are tested for viral markers and found to be non-reactive. This sera yields consistently negative FCXM results.

Following this incubation, cells were washed with a wash buffer containing DPBS and 1% fetal bovine serum (FBS, Gemini Bio-products, West Sacramento, Calif., USA). The cells were resuspended in wash buffer and transferred to separate tubes containing a lyophilized custom cocktail of differentially-labeled antibodies that specifically recognize the various IgG subclasses (obtained from BD Lyotube, BD Pharmingen, San Jose, Calif., USA). Incubation of donor cells with the lyophilized antibody cocktail was carried out in the dark for 20 minutes, and the cells were then washed with wash buffer to remove the excess antibody.

The specific anti-HLA IgG subtype antibodies bound to the cells were detected using a multi-color flow cytometry detection method described herein. IgG subtype levels in patient serum was compared to the levels observed in the Negative control serum. The fold change in the IgG subtype levels in the patient serum over Negative control serum was calculated. Levels of IgG subtypes in the Patient sera that were 2-fold above the levels in the Negative control serum were designated as positive for that subtype.

Example 2

Protocol for Identification of IgG Subtypes by Flow Cytometry

The following description is similar to the procedures described in Example 1, with some minor variations.

Isolate PBMC from whole blood or using frozen PBMC.
Wash twice with phosphate-buffered saline (PBS, pH 7.4) and perform a viability count.
Centrifuge at 1500 rpm for 5 minutes.
Discard the supernatant and resuspend the cell pellet in 0.3 ml FcR blocker reagent per $10^7$ cells (Innovex Cat # NB309).
Incubate at room temperature (ca. 20 degrees Celsius) for 10 minutes.
Wash with excess PBS twice.
Resuspend the cells in $10^7$ cells/ml in staining buffer (i.e., phosphate-buffered saline, pH 7.4, containing 5% v/v fetal bovine serum).
Aliquot 100 microliters per test ($10^6$ per test) of cell suspension to each 12×75 mm tube.
Add 20 microliters neat serum to each tube.
Incubate at 4 degrees Celsius for 30 minutes.
Wash with 2.5 ml staining buffer.
Discard the supernatant.
Resuspend in 100 microliters staining buffer and transfer the content to the lyotube.
Incubate at room temperature for 20 minutes.
Wash with 2.5 ml staining buffer.
Discard the supernatant and resuspend in 0.4 ml staining buffer.
Acquire the sample, measuring amounts of individual IgG subtypes.

Example 3

Using IgG Subtyping in Heart Transplantation Across a Positive Flow-Cytometry Cross Match (FCXM)

A positive FCXM is often a deterrent to heart transplantation due to the risk of hyperacute rejection and antibody-mediated rejection (AMR). While highly sensitive to the presence of donor-specific antibodies, FXCM does not determine whether these antibodies bind complement or not.

Case Report: 61 year old African-American male with coronary artery disease developed following myocardial infarction and coronary artery bypass graft, who developed heart failure due to ischemic cardiomyopathy with ejection fraction (EF) 15-20%. Due to progressive symptoms despite medical therapy and implantation of a cardiac resynchronization therapy device, he had a Heart Mate II left ventricular assist device (LVAD) implanted as a bridge to transplant. Post-LVAD course was complicated by recurrent gastrointestinal bleed requiring multiple transfusions as well as a driveline exit site infection. He was upgraded to status 1A but unable to get a donor due to high panel reactive antibodies (PRAs)—Class I 69%, Class II 3%. Desensitization was attempted using plasmapheresis, intravenous immunoglobulin, rituximab, mycophenolate and bortezimib with no significant response.

A suitable donor was identified with a negative complement-dependent cytotoxicity result on prospective cross matching. However, FCXM was strongly positive for both T- and B-cells (median channel shift: T-cell 362/50, B-cell 359/100). Recipient serum analysis was performed using custom antibodies that recognize the different IgG subtypes. Of the 4 IgG subtypes, only subtypes 2 and 4 were identified in the recipient's serum. Since only IgG subtypes 1 and 3 are known to be complement-binding, it was felt safe to proceed with transplant.

Heart transplantation was performed and recipient received induction immunosuppressive therapy ("induction therapy") with basiliximab as well as protocol immunosuppression with prednisone, tacrolimus and mycophenolate. He had normal graft function immediately post-op with no hyperacute rejection. Repeat echo done 12 days post-transplant showed normal biventricular function. He had 14 protocol endomyocardial biopsies over 12 months with no significant cellular rejection seen. Staining of all specimens for C4d and CD68 did not show evidence of antibody-mediated rejection. He continues to do well with preserved graft function EF 70% at his first annual visit. A regadenoson stress test performed at that time showed no evidence of ischemia.

Described in this example is a case where IgG subtyping was utilized to proceed with heart transplantation despite a positive FCXM. The absence of complement-binding IgG subtypes 1 and 3 on recipient serum led to a successful heart transplant without occurrence of rejection and normal graft function at 1 year.

Example 4

Method of Preparing a Reagent Suitable for Simultaneous Flow Cytometric Identification of Four IgG Subtypes 1. Purchase individual anti-IgG 1, 2, 3, 4 antibodies (Abs) that are fluorescently labeled from different companies and determine the clones of these Abs.

2. Assess each clone to be suitable for the experiment (binding of the secondary anti-IgG Ab to the primary Ab attached to the HLA antigen (Ag) on PBMC).

3. Determine amount of each secondary anti-IgG Ab that needs to be included in the reagent. This requires performing the experiment individually with each anti-IgG Ab.

4. Perform the experiment with combinations of the 4 anti-IgG Abs (in groups of 2, 3 or all 4 together) and determine if there is any steric hindrance that prevents binding of the secondary Abs to the primary Abs that are bound to the HLA Ag on PBMCs. If so, select one or more different Abs in place of at least one of the sterically hindered Abs.

5. Select a reagent for blocking the Fc receptor as a backup. The reagent currently used is the "Fc Receptor Blocker" which is commercially available, as described above, and works as per expectations. Others are known in the art.

6. Obtain "Standard Beads" that are labeled with individual IgG subtypes for use as internal experimental standards to be run with each experiment.

7. Perform the standardization of the above reagents with Standard Beads and freshly isolated PBMCs. Standardization of reagents entails performing multiple experiments using the same concentration of anti-IgG Abs in combination as determined above with the same amount of Standard Beads but using PBMCs isolated from various donors. This demonstrates that there is consistency in the results with Standard Beads for each experiment performed and that this assay can detect IgG subtype levels bound to PBMCs isolated from various donors.

8. Validate the above standardized experiment using freshly isolated PBMCs from multiple donors (e.g., 20 or more donors).

Each of these steps is preferably document so that details are available for inspection by regulatory agencies, if necessary or desirable.

Example 5

An IgG Subtype Specific Flow Crossmatch Assay Can Increase the Number of Successful Transplants in Sensitized Renal Recipients A positive flow cytometric crossmatch (FXCM) is considered a contraindication to a successful renal transplant. The standard FXCM does not distinguish between the various subtypes of the immunoglobulin molecule (IgG1, IgG2, IgG3, and IgG4). Only IgG1 and IgG3 subtypes are capable of maximal complement activation. IgG2 and IgG4 are relatively benign. We present preliminary results from our study evaluating a new FCXM test that specifically detects and quantifies IgG subtypes responsible for a positive crossmatch.

The methods used in the experiments described in this Example are now described. Pre-transplant sera from 7 recipients and blood samples from their respective donors were evaluated. IgG subtype analysis was carried out using the FCXM. PBMCs isolated from the donor samples were incubated with the patient and control sera. The cells were then incubated in the lyophilized custom cocktail of antibodies that specifically recognize the various IgG subtypes bound to the cells, followed by FCXM analysis. C1q (complement activation) testing on all sera was carried out.

The results of these experiments were as follows. Standard FCXM were positive in most of the cases studied (5/7) and a transplant would therefore normally not have been conducted based on those results alone. However, using the IgG subtyping assay described herein, we were able to determine that the positive crossmatch result was attributable to the presence of non-complement binding IgG2 or IgG4 antibodies and that the transplant could be performed. There was almost complete agreement between the IgG subtyping and C1q results. All cases showed the presence of non-complement activating antibodies as responsible for the positive FCXM (except CF). CFL showed the presence of IgG3 antibodies with a negative C1q; probably the result of denatured antibodies. There were no episodes of clinical rejection observed in any of the cases or requirement for dialysis in the first week for any of the recipients. These results are summarized in the table illustrated in FIG. 1. In FIG. 1, "Cr." refers to serum creatine determination.

The experiments described in this Example demonstrate that we have developed an IgG subtype FCXM assay that has the ability to identify presence of complement activating antibodies. This assay has shown itself to be highly accurate in detecting the IgG subtype(s) causing a positive flow crossmatch. The use of this assay could potentially result in successful transplants even in the presence of a positive FCXM for highly sensitized recipients.

Example 6

Increasing Successful Transplants in Sensitized Heart and Renal Recipients Using a New Flow Crossmatch Assay to Distinguish Between IgG Subtype(s)

Transplant programs are reluctant to carry out transplantation in the presence of a positive flow crossmatch. The standard Flow Cytometric Crossmatch (FCXM) does not discriminate between the various subtypes of the immunoglobulin molecule (IgG1, IgG2, IgG3, and IgG4). We have developed a new FCXM assay that is able to specifically detect and quantify the amount of complement-activating (IgG1 and IgG3) and non-complement activating (IgG2 and IgG4) IgG antibodies. We present preliminary results using this assay in two separate models for heart and kidney transplantation. We demonstrate that successful transplantation in the presence of a positive crossmatch can be accomplished using this assay that has the ability to distinguish between the various IgG subtypes.

The methods used in the experiments described in this Example are now described. Pre-transplant sera from 7 heart recipients (including the one described in Example 3) and 7 kidney recipients and blood samples from their respective donors were used for this study. IgG subtype analysis was carried out using the FCXM. PBMCs isolated from the donor samples were incubated with the patient and control sera. The cells were then incubated in the lyophilized custom cocktail of antibodies that specifically recognize the various IgG subtypes bound to the cells, followed by FCXM analysis. C1q testing was carried out on all sera.

Results obtained for the kidney recipient patients are described in Example 5 and FIG. 1.

Figure 2:
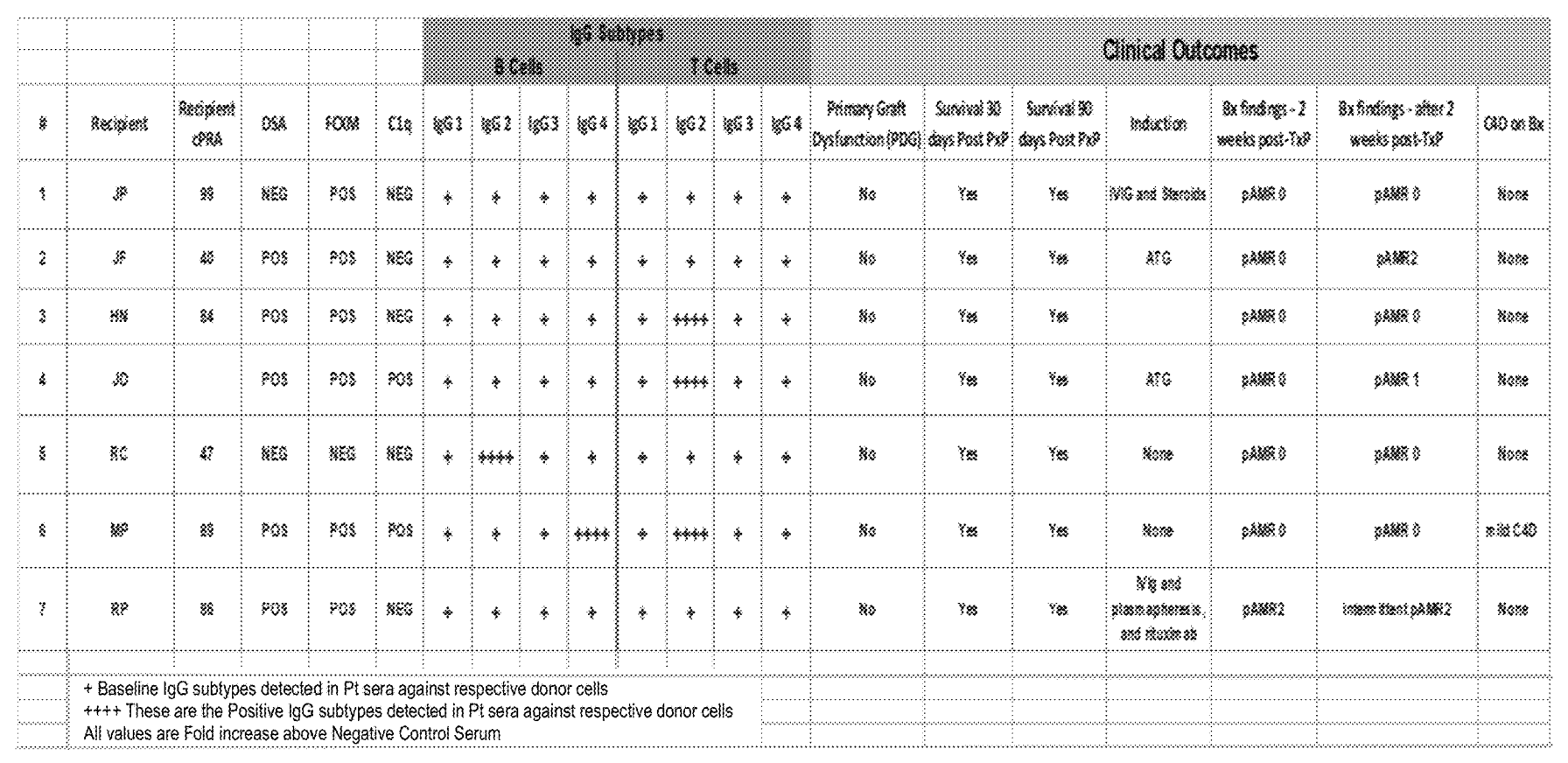

Results obtained for the heart recipient patients were as follows. A majority of the heart transplant cases studied (6/7) had a positive crossmatch, and a transplant would therefore normally not have been conducted. However, using the IgG subtyping assay described herein, we were able to determine that the positive crossmatch result was attributable to the presence of non-complement binding IgG2 or IgG4 antibodies and that the transplant could be performed. C1q results were in agreement with crossmatch results in most of these cases. Two cases (JO, MP) were positive for C1q; probably due to prozone effect of HLA-specific IgM antibodies. All cases had positive 30-day and 90-day survival post-transplant with no primary graft dysfunction or >2R rejection (using the terminology of the International Society of Heart and Lung Transplantation Guidelines for the Care of Heart Transplant Recipients). Two cases (JF, RP) who had documented antibody-mediated rejection and were treated with induction therapy continued to have normal graft function. These results are summarized in the table illustrated in FIG. 2.

The experiments described in this Example and in Example 5 demonstrate that the IgG subtype assay described herein is highly accurate for detecting the IgG subtype(s) causing a positive flow crossmatch. These results demonstrate for the first time that the assay can facilitate safe transplants even in the presence of a normally contraindicating standard positive flow cross-match. Clinical implementation of our IgG subtypes assay can have a great impact on increasing the number of successful transplants carried out, especially in sensitized recipients.

The disclosure of every patent, patent application, and publication cited herein is hereby incorporated herein by reference in its entirety.

While this subject matter has been disclosed with reference to specific embodiments, it is apparent that other embodiments and variations can be devised by others skilled in the art without departing from the true spirit and scope of the subject matter described herein. The appended claims include all such embodiments and equivalent variations.

What is claimed is:

1. A method of grafting a tissue obtained from a potential vertebrate donor to a potential recipient, the method comprising:
    inhibiting Fc receptors situated on peripheral blood mononuclear cells obtained from the potential donor from non-specific antibody binding,
    after the inhibiting step, contacting the peripheral blood mononuclear cells obtained from the potential donor with antibodies in a sample of a body fluid obtained from the potential recipient,
    contacting the antibodies of the potential recipient with differentially labeled antibodies that specifically recognize antibodies of at least IgG subtypes IgG1 and IgG3,
    detecting a degree of binding between the peripheral blood mononuclear cells of the potential donor and the antibodies of at least IgG subtypes IgG1 and IgG3 of the potential recipient in excess of a basal level of binding, and
    grafting the tissue obtained from the potential donor to the potential recipient if substantially no binding between the peripheral blood mononuclear cells of the potential donor and the antibodies of IgG subtypes IgG1 and IgG3 of the potential recipient in excess of the basal level of binding is detected,
    wherein the potential donor is a human.

2. The method of claim 1,
    wherein contacting the antibodies of the potential recipient comprises contacting the antibodies of the potential recipient with differentially labelled antibodies that specifically recognize antibodies of at least IgG subtypes IgG1, IgG2, IgG3, and IgG4; and
    wherein detecting the degree of binding comprises detecting the degree of binding between the peripheral blood mononuclear cells of the potential donor and the antibodies of at least IgG subtypes IgG1, IgG2, IgG3, and IgG4 of the potential recipient in excess of the basal level of binding.

3. The method of claim 2, wherein the detecting the degree of binding step is performed in a single assay.

4. The method of claim 1, wherein the step of contacting the antibodies of the potential recipient with differentially-labeled antibodies that specifically recognize antibodies of at least IgG subtypes IgG1 and IgG3 comprises distinguishing between antibodies of IgG subtypes IgG1 and IgG3.

5. The method of claim 2, wherein the step of contacting antibodies of the potential recipient with differentially-labeled antibodies that specifically recognize antibodies of at least IgG subtypes IgG1, IgG2, IgG3, and IgG4 comprises distinguishing between antibodies of IgG subtypes IgG1, IgG2, IgG3, and IgG4.

6. The method of claim 5, further comprising contacting the peripheral blood mononuclear cells obtained from the potential donor with differentially-labeled antibodies that distinguishably recognize B and T cells of the potential donor.

7. The method of claim 1, wherein individual peripheral blood mononuclear cells obtained from the potential donor are detected using flow cytometry after contacting the peripheral blood mononuclear cells obtained from the potential donor with the antibodies in the sample of the body fluid obtained from the potential recipient.

8. The method of claim 2, wherein individual peripheral blood mononuclear cells obtained from the potential donor are detected using flow cytometry after contacting the peripheral blood mononuclear cells obtained from the potential donor with the antibodies in the sample of the body fluid obtained from the potential recipient and after contacting the antibodies of the potential recipient with differentially-labeled antibodies that specifically recognize antibodies of at least IgG subtypes IgG1, IgG2, IgG3, and IgG4.

9. The method of claim 2, wherein individual peripheral blood mononuclear cells obtained from the potential donor are detected using flow cytometry after contacting the peripheral blood mononuclear cells obtained from the potential donor with the antibodies in the sample of the body fluid obtained from the potential recipient, after contacting the antibodies of the potential recipient with differentially-labeled antibodies that specifically recognize antibodies of at least IgG subtypes IgG1, IgG2, IgG3, and IgG4, and after contacting the peripheral blood mononuclear cells obtained from the potential donor with differentially-labeled antibodies that distinguishably recognize B and T cells of the potential donor.

10. The method of claim 1, wherein the potential recipient is a vertebrate.

11. The method of claim 1, wherein the potential recipient is a human.

12. The method of claim 1, wherein the peripheral blood mononuclear cells obtained from the potential donor have not irreversibly lost capacity for cellular function at the time they are contacted with the antibodies in the sample of the body fluid obtained from the potential recipient.

13. The method of claim 1, wherein the detecting the degree of binding step is performed in a single assay.

* * * * *